(12) United States Patent
Grinfeld et al.

(10) Patent No.: US 7,879,083 B2
(45) Date of Patent: Feb. 1, 2011

(54) STENT FOR OSTIAL LESIONS AND VASCULAR BIFURCATIONS

(76) Inventors: Liliana Rosa Grinfeld, Avda. del Libertador 7680, 6th floor, (1429) Buenos Aires (AR); Roberto Rafael Grinfeld, Avda. del Libertador 7680, 6th floor, (1429) Buenos Aires (AR)

( * ) Notice: Subject to any disclaimer, the term of this patent is extended or adjusted under 35 U.S.C. 154(b) by 692 days.

(21) Appl. No.: 11/111,280

(22) Filed: Apr. 20, 2005

(65) Prior Publication Data
US 2006/0224233 A1 Oct. 5, 2006

(30) Foreign Application Priority Data
Apr. 3, 2005 (AR) .............................. 20050100823

(51) Int. Cl.
*A61F 2/06* (2006.01)
*A61F 2/82* (2006.01)
(52) U.S. Cl. ................. 623/1.16; 623/1.35; 606/155
(58) Field of Classification Search ............... 623/1.16, 623/1.2, 1.3; 606/155–156
See application file for complete search history.

(56) References Cited

U.S. PATENT DOCUMENTS

| | | | | |
|---|---|---|---|---|
| 5,366,462 A | * | 11/1994 | Kaster et al. | ................. 606/153 |
| 5,540,712 A | * | 7/1996 | Kleshinski et al. | ......... 623/1.19 |
| 5,776,161 A | * | 7/1998 | Globerman | .................. 606/194 |
| 6,527,799 B2 | * | 3/2003 | Shanley | ..................... 623/1.15 |
| 6,602,282 B1 | * | 8/2003 | Yan | ............................. 623/1.15 |
| 6,656,220 B1 | * | 12/2003 | Gomez et al. | .............. 623/1.15 |
| 6,663,664 B1 | * | 12/2003 | Pacetti | ......................... 623/1.2 |
| 6,749,628 B1 | * | 6/2004 | Callol et al. | ................ 623/1.15 |
| 6,942,689 B2 | * | 9/2005 | Majercak | .................... 623/1.15 |
| 7,022,131 B1 | * | 4/2006 | Derowe et al. | ............. 623/1.11 |
| 7,195,640 B2 | * | 3/2007 | Falotico et al. | ............. 623/1.42 |
| 2002/0193862 A1 | * | 12/2002 | Mitelberg et al. | ............ 623/1.2 |
| 2004/0092977 A1 | * | 5/2004 | Vargas et al. | ................. 606/155 |
| 2004/0138730 A1 | * | 7/2004 | Mitelberg et al. | ............ 623/1.2 |
| 2005/0038455 A1 | * | 2/2005 | Bates et al. | .................. 606/153 |
| 2005/0288693 A1 | * | 12/2005 | Suyker et al. | ................ 606/153 |

* cited by examiner

*Primary Examiner*—Bruce E Snow
*Assistant Examiner*—Melissa Hoban
(74) *Attorney, Agent, or Firm*—Bachman & LaPointe, P.C.

(57) ABSTRACT

A stent for ostial lesions and vascular bifurcations has a tubular body comprised by a succession of sections of skeletal members. In one or both end rows of the tubular body, there are expansive bending devices comprising sectional weakenings and open extremities. In the case of the end row, by a proper expander balloon, expansive bending of longitudinal branches of the end row may be produced. Bending is produced due to sectional weakenings. Open extremities allow producing the expansion in a way such as the flourishing of a flower bloom. Under such conditions, bending of the end row makes possible the adequate coverage of the ostial or bifurcation lesion affecting wall of the application vascular conduit.

9 Claims, 2 Drawing Sheets

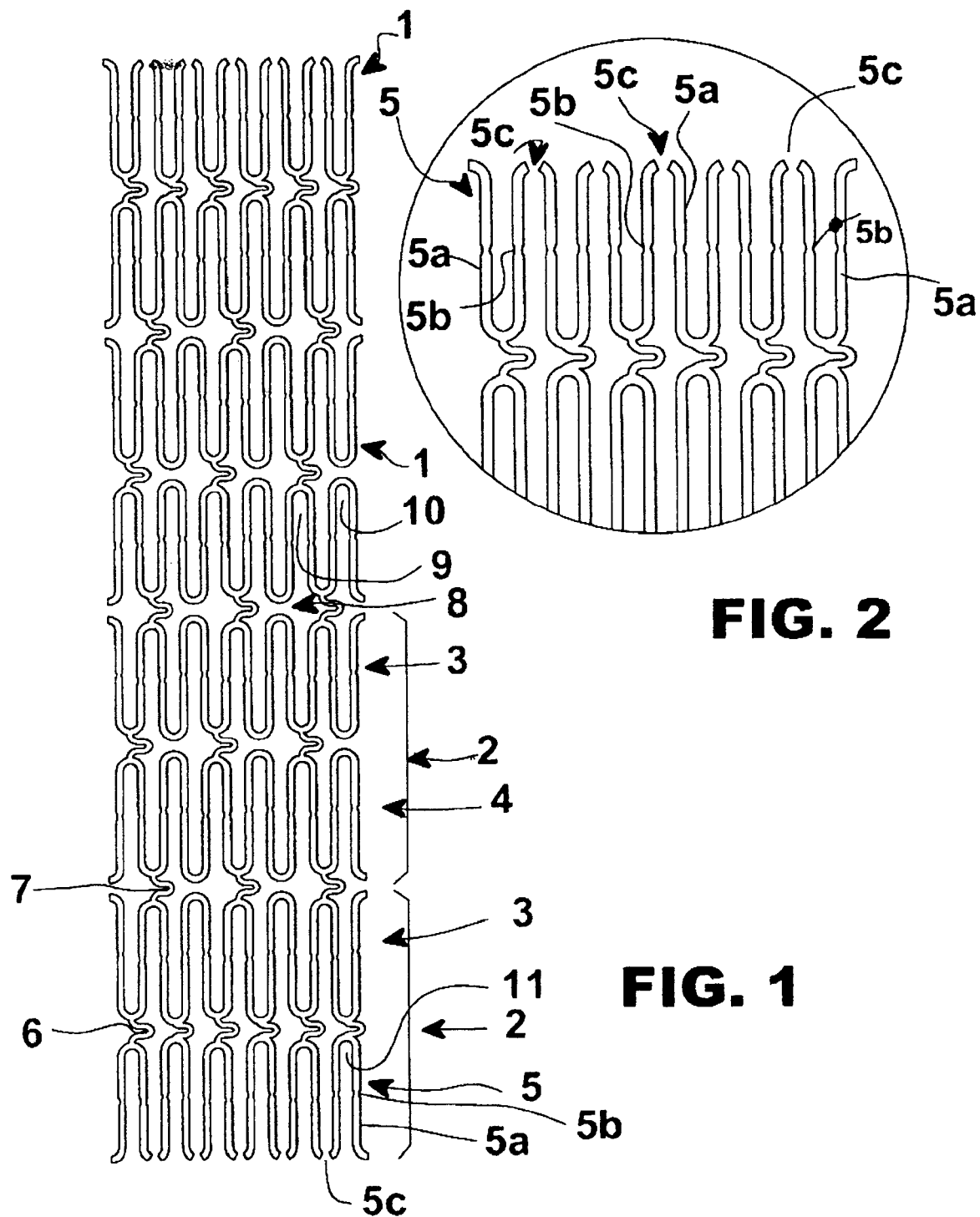

STENT FOR OSTIAL LESIONS AND VASCULAR BIFURCATIONS

BACKGROUND OF THE INVENTION (1) Field of the Invention

The instant invention relates to a stent for ostial lesions and vascular bifurcations the extremities of which allow a side unfolding totally covering such lesions.

(2) Prior Art

As already known, the most used endovascular treatments at present are those carried out through the interior of the clearance of vascular conduits, instead of using the traditional method of accessing such conduits by means of a surgery allowing access to the affected artery or vein.

Such endovascular treatments are effected into the vessel clearance, with different purposes and using different means, as follows:

to produce dilatation of the artery or vein, to dissolve thrombi inside the artery or vein, to close abnormal communications between these vessels, between such conduits or communication to neighbor tissues, to coat surfaces thereof with a prosthesis, such as a "sleeving", to return the normal gage to a dilated artery (aneurysm), to insulate the inner surface of an artery from blood physical or chemical elements, after effecting a balloon dilatation (inner "bypass"), etc.

Based on the work of US radiologist Charles Dotter, and within endovascular techniques, endovascular placing of expanders has been an important improvement, specially permeable and resilient tubular structures normally known as "stents".

Therefore, in the present specification, the term "stent" is applied to those devices which may be also referred to as endovascular "expanders".

The "stents"—generally made from special metallic frameworks—form expansible skeletal tubes, generating radial forces capable of maintaining the vessels open and counteracting tensions tending to close them.

Essentially, it may be said that there are three kinds of vascular "stents":: thermo-sensitive stents, which adopt predetermined shapes at different temperatures, particularly that of the human body (as those of Nitinol series; of U.S. Pat. No. 4,425,908, etc.); expansible stents with balloon (such as disclosed in European Patent EP 378,151); and resiliency auto-expansible stents (as disclosed in U.S. Pat. No. 4,580,568).

Vascular "stents" are being used in angioplasty (with increasing frequency) thus attaining an improvement in the immediate and long term results; for treating dissections after angioplasty and for assuring endoluminal grafts, as well as improvement in the quality of various prosthetic applications, (Perrone, R et al, "Prótesis endoluminal" (Endoluminal Prosthesis), Rev. Arg. de Cirugía", 1992; 62:146-149; Mazzariello, R: "Aplicación percutanea de prótesis biliar expandible" (Percutaneous application of expansible bile prosthesis), Revista Argentina de Cirugía, 1990: 979-983; etc.)

Besides, combined stents or expanders and grafts have been used in several applications, such as: aneurysms, dissections, vascular trauma and arterial occlusion diseases.

Calcified arteries represent a serious problem for intervening cardiologists trying to dilate such arteries by placing stents. Also, there is an important percentage of failures in the results expected from this kind of operations.

More particularly, cases of lesions such as arterial lesions and bifurcation lesions are till now a challenge for interventionalcardiologists or other specialists working in the field of angioplasties.

In fact, the percentage of failures and re-stenosis is very much higher than that obtained with these treatments in other vascular territories. This is due to the fact that expanding devices such as stents, which properly cover ostial or bifurcation zones in the arterial tree have as yet not been developed.

SUMMARY OF THE INVENTION

The mentioned disadvantages are solved by means of the stent of the invention the end row of which may be expansively bent and expanded as a flourishing flower bloom.

Therefore, expansive bending allows that part of the stent to be attached, thus covering the ostium or bifurcation affected by the lesion. This is accomplished by using a proper expander balloon capable of producing a larger dilatation in the zone of the end row.

Finally, the stent of the invention has an excellent capability to be adapted to the complex morphology of vascular regions such as those described.

BRIEF DESCRIPTION OF THE DRAWINGS

A preferred exemplary embodiment of the invention is described, without limitation purposes, in connection with the accompanying drawings, wherein:

FIG. 1 is a side elevation view of the stent walls development, wherein the succession of regions comprising the cited walls, the engaging bridges and the appearance of the end rows may be seen.

FIG. 2 is a side elevation view corresponding to a detail of the end row in which the means—section weakenings and open extremities permitting its expansive accommodation—are shown.

DETAILED DESCRIPTION OF THE PREFERRED EMBODIMENT(S)

Figure 3:
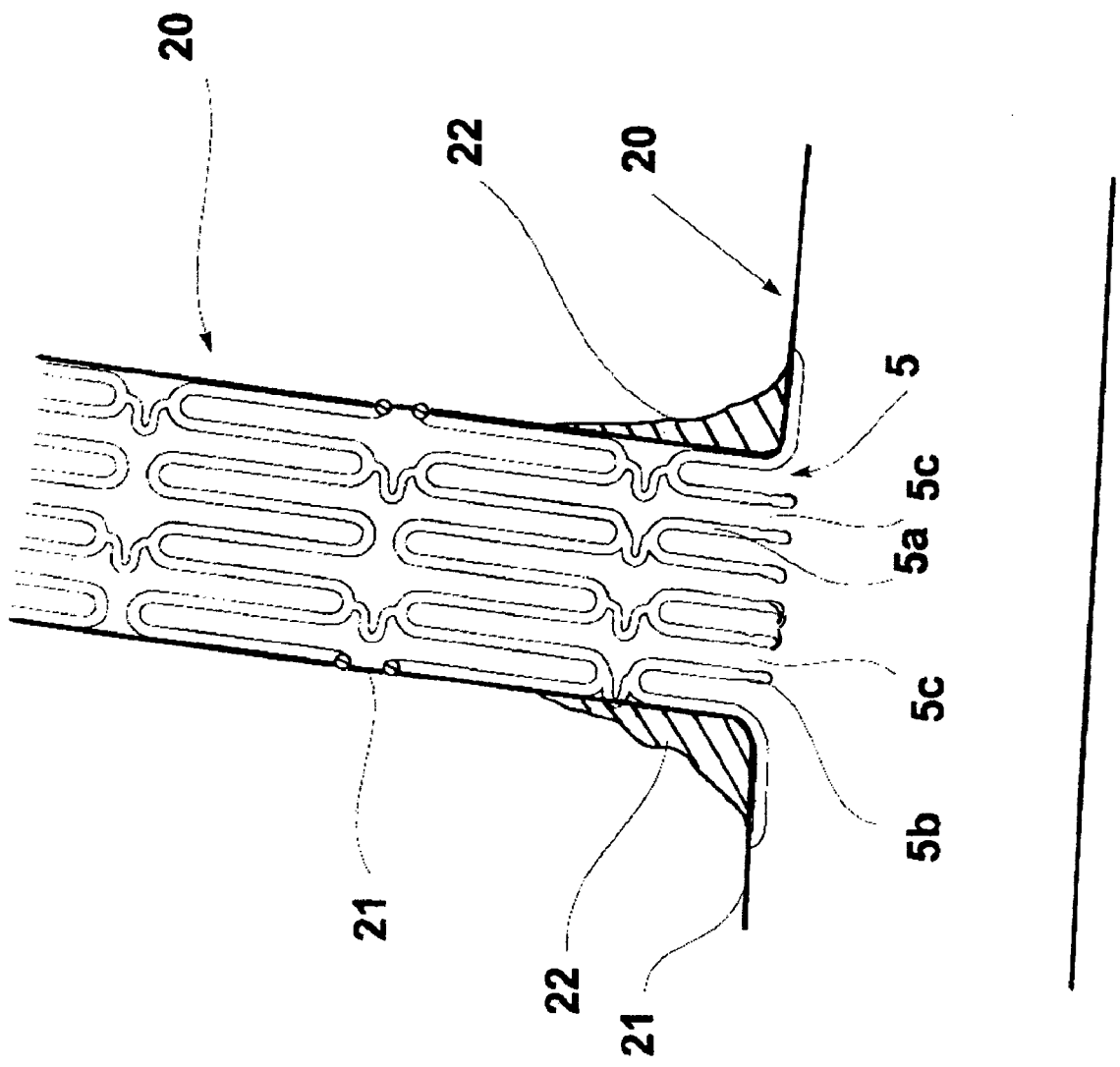
FIG. 3 is a cross section of the application vascular conduit showing the way in which the end row is placed once the expansive bending is effected.

In different figures, the same reference numbers and/or letters indicate the same or corresponding parts.

LIST OF THE MAIN REFERENCES (1) Tubular body of the stent
(1a) Skeletal members forming the tubular body (1).
(2) Sections of the tubular body.
(3) First row of each section (2).
(4) Second row of each section (2).
(5) End row.
(5a) Longitudinal branches of the end row (5).
(5b) Sectional weakening [means for expansive bending]
(5c) Open extremities [means for expansive bending]
(6) First simple engaging bridges [between first (3) and second (4) rows].
(7) Second engaging bridges [between sections (2)].
(8) Separation between sections (2) and rows (3) (4).
(9) Short entrance.
(10) Long entrance.
(11) Outer entrance
(20) Application vascular conduit

(21) Vascular walls [endothelium]
(22) Lesion.

The stent for vascular ostial and bifurcation lesions (22) constituted by a tubular body (1)—generally formed by a metal framework—which, subjected to the action of an expansion balloon is capable of exerting tension in the direction of its diametrical expansion until its outer surfaces press against the endothelium of the application vascular conduit (20), defining an endovascular positioning which maintains or increases the clearance of said conduit (20), comprising:

A tubular body (1) constituted by a succession of sections (2) the framework of which is festoon shaped;

Each festoon shaped section (2) is comprised by rows (3) (4) (5) of entrances (9) (10) (11) and projections;

Sections and rows are engaged by means of engaging bridges; the stent being characterized in that:

At least one of the end rows (5) comprises means (5b) (5c) affording expansive bending capacity; and Said expansive bending forms the portion to be attached to the ostial or bifurcation lesion (22).

In general, the instant invention is comprised by a stent having high fixation capacity and endothelial contact comprising a tubular body (1) constituted by a succession of sections (2) of skeletal members. In one or both end rows (5) of the tubular body (1) there are means for expansive bending which comprise sectional weakenings (5b) and open extremities (5c). In the case of the end row (5), by means of a proper expander balloon, expansive bending of longitudinal branches (5a) of said end row (5) may be attained. Bending is produced by sectional weakenings (5b). Open extremities (5c) allow the expansion to be produced as the flourishing of a flower bloom. Under such conditions, bending or the end row (5) enables the proper coverage of the ostial or bifurcation lesion (22).

More particularly, the stent has a tubular body (1) structured by a framework of skeletal members made of a suitable metallic material which, under the influence of the expansion balloon, may exert tension in the direction of its diametrical expansion against the endothelium (21) of the application vascular conduit, such that its endovascular positioning is capable of maintaining or increasing the clearance of said conduit (20), being fixed to the walls thereof (21).

In one embodiment, the skeletal members of the tubular body (1) of the stent form a succession of tubular sections (2)—as component functional units—whose framework is festoon shaped. This is due to the fact that each section (2) is constituted by two rows (3) (4) of entrances (9) (10) and projections, unequal and opposed, whose sinuosities determine said festoon shape.

In each section, both rows (3) (4) are partially joined by means of curved shaped first engaging bridges (6). Between bridge (6) and bridge (6), rows (3) (4) have approximation zones, although they always maintain a small separation (8) [e.g. 30 microns]. Therefore, while the first bridges (6) determine the partial union of rows (3) (4) at some points, separations (8) determine the partial separation thereof (3) (4) in other sectors.

On the other hand, sections (2) adjacent tubular body (1) are partially joined to each other by means of second engaging bridges (7). Also in this part there are approximation zones, although a small separation (8) [e.g. 30 microns] is maintained. Consequently, while the second bridges (7) determine the partial union of sections (2) adjacent in some points, separations (8) determine the partial separation in other points.

This partial union through engaging bridges (7) (6), which alternate with separations (8)—between rows (3) (4) as well as between adjacent sections (2)—constitutes a resilient means for the tubular body (1) of the stent.

The tubular body may properly operate with sections (2) engaged by means of three second bridges (7), on one part, and with rows (3) (4) engaged by means of three first bridges (6).

At one or both end rows (5) of the tubular body (1) there are expansive bending means.

In the present embodiment, these means comprise sectional weakenings (5b) and open extremities (5c).

These sectional weakenings (5b) may be placed, for example, in the longitudinal branches (5a) of end rows (5).

Said sectional weakenings (5b) may be thinness regions surrounding, partially or completely, said longitudinal branches (5a), always with the object of permitting their expansive bending.

On their part, open extremities (5c) are placed to interrupt the continuity between longitudinal branches (5a).

Also, the inclusion of depressions [not shown] along rows (3) (4) (5) has been foreseen. These may be used for transferring drugs to the endothelium (22).

Operation

Rows (3) (4) (5) of each section (2) as well as adjacent sections (2) are partially joined to each other by means of first (6) and second (7) engaging bridges, respectively.

Further, between bridge and bridge of the festoon shaped framework there are separations (8) [of about 30 microns], such that this combination of means affords resiliency to the tubular body (1) of the stent. This resiliency allows elastic deformations accompanying the behavior of walls (21) of the application vascular conduit (20).

In the case of the end row (5), by means of a proper expander balloon, expansive bending of longitudinal branches (5a) of said end row (5) may be obtained. Bending is produced by sectional weakenings (5b). Open extremities (5c) allow producing the expansion as the flourishing of a flower bloom.

Under such conditions, bending of the end row (5) enables the proper coverage of the ostial or bifurcation lesion (22) which affects wall (21) of vascular conduit (20).

It is obvious that various modifications may be apparent to one skilled in the art in the light of the foregoing, without departing from the main principles of the invention which are clearly contained in the appended claims.

What is claimed is:

1. A stent for vascular ostial and bifurcation lesions constituted by a tubular body formed by a metal frame work formed by a succession of sections comprised by rows of entrances and projections, each of said rows being linked and separated by engaging bridges, at least one end row comprising means for providing expansion and bending capacity capability; and said means for providing expansion and bending capability comprising a plurality of independent U-shaped members forming said at least one end row; each said U-shaped member having a pair of legs; each said leg having a free end; and each said leg having means for forming a portion to be attached to the ostial or bifurcation lesion comprising sectional weakenings.

2. The stent for vascular ostial and bifurcation lesions as claimed in claim 1, wherein said sectional weakenings are positioned in longitudinal branches of said legs.

3. The stent for vascular ostial and bifurcation lesions as claimed in claim 1, wherein said sectional weakenings are constituted by thinness regions in said legs which allow said legs to bend against said ostial or bifurcation lesion.

4. The stent for vascular ostial bifurcation lesions as claimed in claim 3, wherein said sectional weakenings are further constituted by entrances surrounding, partially or completely, said legs.

5. The stent for vascular ostial and bifurcation lesions as claimed in claim 1, wherein each said U-shaped member has an open extremity between the legs.

6. The stent for vascular ostial and bifurcation lesions of claim 1, wherein each of said plurality of rows other than said at least one end row are formed by serpentine shaped members.

7. A stent for vascular ostial and bifurcation lesions comprising:

a tubular body formed by a metal frame work formed by a succession of sections comprised by rows of entrances and projections;

said tubular body having a longitudinal axis;

each of said rows being linked and separated by engaging bridges, said tubular body having an end row formed by a plurality of independent U-shaped members;

each said U-shaped member having a pair of legs which extend parallel to said longitudinal axis;

each said leg having a free end;

and each said leg having a sectional weakening which allows a portion of said leg to bend relative to said longitudinal axis so that said leg portion is attached to the ostial or bifurcation lesion.

8. The stent of claim 7, wherein each said U-shaped member has a curved portion connecting said two legs and an opening between said legs.

9. The stent of claim 7, wherein said leg portion bends from said sectional weakening to said free end relative to said longitudinal axis to position said free end adjacent to said ostial or bifurcation lesion.

* * * * *